(12) United States Patent
Starke et al.

(10) Patent No.: US 10,520,406 B2
(45) Date of Patent: Dec. 31, 2019

(54) TENSILE SPECIMEN, METHOD FOR PRODUCING A TENSILE SPECIMEN, DEVICE FOR CARRYING OUT A TENSILE TEST, AND METHOD FOR CARRYING OUT A TENSILE TEST

(71) Applicant: Airbus Defence and Space GmbH, Taufkirchen (DE)

(72) Inventors: Peter Starke, Ottobrunn (DE); Harald Kraft, Malsch (DE); Martin Holzapfel, Stuttgart (DE); Marcel Brodbeck, Stuttgart (DE)

(73) Assignee: Airbus Defence and Space GmbH, Taufkirchen (DE)

( * ) Notice: Subject to any disclaimer, the term of this patent is extended or adjusted under 35 U.S.C. 154(b) by 0 days.

(21) Appl. No.: 15/359,121

(22) Filed: Nov. 22, 2016

(65) Prior Publication Data
US 2017/0153170 A1    Jun. 1, 2017

(30) Foreign Application Priority Data
Nov. 26, 2015    (DE) .......................... 10 2015 223 404

(51) Int. Cl.
*G01N 3/08* (2006.01)
*G01N 3/02* (2006.01)
*G01N 3/04* (2006.01)

(52) U.S. Cl.
CPC ................ *G01N 3/08* (2013.01); *G01N 3/02* (2013.01); *G01N 3/04* (2013.01);
(Continued)

(58) Field of Classification Search
CPC .. G01N 3/08; G01N 3/02; G01N 3/04; G01N 2203/0405; G01N 2203/028; G01N 2203/0017
(Continued)

(56) References Cited

U.S. PATENT DOCUMENTS 3,660,887 A * 5/1972 Davis ...................... B29C 39/10
174/176
3,664,764 A * 5/1972 Davies et al. .......... B29C 70/04
416/220 A (Continued)

FOREIGN PATENT DOCUMENTS

DE    4116422 A1    11/1992
DE    69628898 T2    5/2004
(Continued)

OTHER PUBLICATIONS

FAT [Forschungsvereinigung Automobiltechnik—Research Association of Automotive Technology], "Dynamic material characteristics for crash simulation," AiF [Arbeitsgemeinschaft industrieller Forschungsvereinigungen—German Federation of Industrial Research Associations], Series No. 211, No. 14205, pp. 1-69, Apr. 24, 2007.
(Continued)

*Primary Examiner* — Jonathan M Dunlap
(74) *Attorney, Agent, or Firm* — Jenkins, Wilson, Taylor & Hunt, P.A.

(57) ABSTRACT

A tensile specimen, in particular a fiber-composite-material tensile specimen, includes a test portion which comprises a fiber material and a tensile stress direction which is predetermined for a material test, and a force-introduction portion, wherein the fiber material in the force-introduction portion extends at least in part along a face which is oriented obliquely to the tensile stress direction.

15 Claims, 11 Drawing Sheets

(52) U.S. Cl.
CPC ............... *G01N 2203/0017* (2013.01); *G01N 2203/028* (2013.01); *G01N 2203/0405* (2013.01)

(58) Field of Classification Search
USPC .................. 73/826, 828, 831, 832, 856–860
See application file for complete search history.

(56) References Cited

U.S. PATENT DOCUMENTS

| | | | | |
|---|---|---|---|---|
| 3,699,623 A * | 10/1972 | Kreider | ............... | B23K 20/2333 29/419.1 |
| 3,716,894 A * | 2/1973 | Kingston | ............... | F16G 11/05 403/275 |
| 3,731,360 A * | 5/1973 | Stone, Jr. | ............... | B23P 15/04 29/889.71 |
| 3,739,457 A * | 6/1973 | Davis | ............... | B29C 39/10 174/176 |
| 3,752,600 A * | 8/1973 | Walsh | ............... | F01D 5/282 415/217.1 |
| 3,942,231 A * | 3/1976 | Whitaker | ............... | B23P 15/04 29/889.7 |
| 4,037,990 A * | 7/1977 | Harris | ............... | F01D 5/3053 416/135 |
| 4,040,770 A * | 8/1977 | Carlson | ............... | C22C 47/00 416/230 |
| 4,080,824 A * | 3/1978 | Starks | ............... | G01N 3/04 73/859 |
| 4,111,606 A * | 9/1978 | Prewo | ............... | C22C 47/00 416/224 |
| 4,343,593 A * | 8/1982 | Harris | ............... | F01D 5/282 416/193 A |
| 4,643,609 A * | 2/1987 | Biass | ............... | F16B 2/14 24/122.3 |
| 4,673,606 A * | 6/1987 | Unden | ............... | B29C 37/0085 428/138 |
| 4,755,076 A * | 7/1988 | Salama | ............... | F16G 11/05 24/122.3 |
| 5,136,755 A * | 8/1992 | Shaw | ............... | F16G 11/05 24/122.6 |
| 5,415,490 A * | 5/1995 | Flory | ............... | F16G 11/05 24/122.6 |
| 5,713,169 A * | 2/1998 | Meier | ............... | E04C 5/122 403/371 |
| 5,735,628 A * | 4/1998 | Short | ............... | F16G 11/05 403/218 |
| 5,904,438 A * | 5/1999 | Vaseghi | ............... | F16G 11/05 29/460 |
| 7,137,617 B2 * | 11/2006 | Sjostedt | ............... | B32B 1/08 254/199 |
| 7,798,014 B2 * | 9/2010 | Ferguson | ............... | G01N 3/08 73/831 |
| 8,100,662 B2 * | 1/2012 | Schreiber | ............... | B29C 70/202 416/230 |
| 8,387,467 B2 * | 3/2013 | Bassot | ............... | G01N 3/56 427/478 |
| 8,430,623 B2 * | 4/2013 | Beckford | ............... | F01D 5/14 415/9 |
| 8,568,082 B2 * | 10/2013 | Beckford | ............... | F01D 5/147 415/9 |
| 9,733,172 B2 * | 8/2017 | Kismarton | ............... | G01N 3/02 |
| 9,840,044 B2 * | 12/2017 | Campbell | ............... | B29C 65/48 |
| 2003/0010966 A1 * | 1/2003 | Sjostedt | ............... | B32B 1/08 254/231 |
| 2004/0083607 A1 * | 5/2004 | Campbell | ............... | B29C 47/003 29/857 |
| 2005/0084379 A1 * | 4/2005 | Schreiber | ............... | B23H 3/00 416/230 |
| 2005/0204555 A1 * | 9/2005 | Campbell | ............... | F16G 11/042 29/874 |
| 2006/0160435 A1 * | 7/2006 | Campbell | ............... | F16G 11/025 439/878 |
| 2008/0187441 A1 * | 8/2008 | Schreiber | ............... | B29C 70/202 416/229 R |
| 2009/0007692 A1 * | 1/2009 | Ferguson | ............... | G01N 3/08 73/831 |
| 2010/0054938 A1 * | 3/2010 | Beckford | ............... | F01D 5/147 416/2 |
| 2010/0263453 A1 * | 10/2010 | Mason | ............... | G01N 3/04 73/826 |
| 2012/0114497 A1 * | 5/2012 | Petersen | ............... | F03D 1/0675 416/241 R |
| 2013/0302170 A1 * | 11/2013 | Booze | ............... | F01D 5/3092 416/219 R |
| 2013/0302173 A1 * | 11/2013 | Booze | ............... | F01D 5/282 416/230 |
| 2014/0144489 A1 * | 5/2014 | Buller | ............... | H01L 31/0422 136/251 |
| 2014/0352451 A1 * | 12/2014 | Kismarton | ............... | G01N 3/02 73/826 |
| 2015/0338325 A1 * | 11/2015 | Kismarton | ............... | G01N 3/02 73/788 |
| 2016/0223445 A1 * | 8/2016 | Campbell | ............... | D07B 1/185 |

FOREIGN PATENT DOCUMENTS

| | | | |
|---|---|---|---|
| DE | 10 2005 058 582 A1 | 6/2007 | |
| GB | 2236546 A * | 4/1991 | ............ F16G 11/05 |
| GB | 2255354 A * | 11/1992 | ............ E04C 5/122 |
| GB | 2279085 A * | 12/1994 | ............ F16G 11/042 |
| JP | 03174077 A * | 7/1991 | |

OTHER PUBLICATIONS

German Office Action for Application No. 10 2015 223 404 dated Jul. 19, 2016.

* cited by examiner

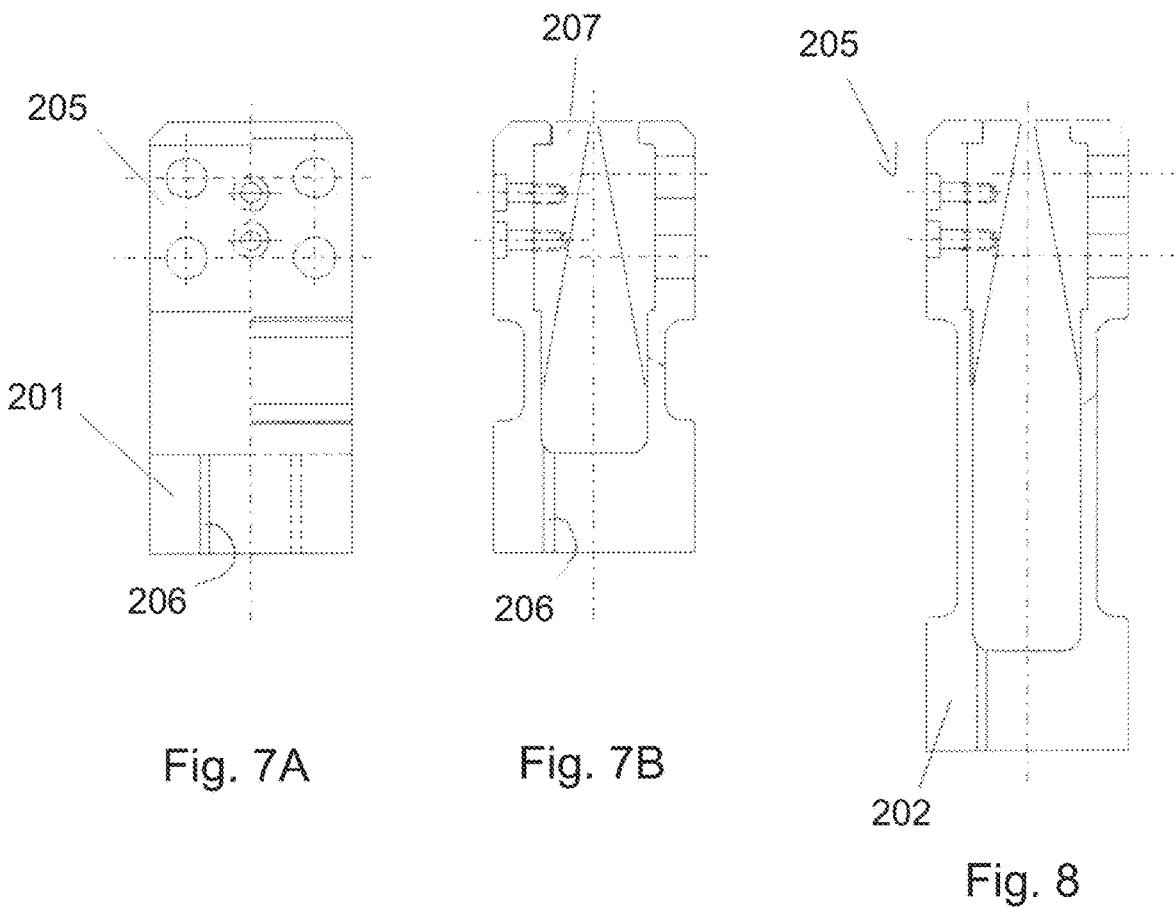

TENSILE SPECIMEN, METHOD FOR PRODUCING A TENSILE SPECIMEN, DEVICE FOR CARRYING OUT A TENSILE TEST, AND METHOD FOR CARRYING OUT A TENSILE TEST

CROSS-REFERENCE TO RELATED APPLICATION

This application claims priority to German Patent Application DE 10 2015 223 404.5 filed Nov. 26, 2015, the entire disclosure of which is incorporated by reference herein.

TECHNICAL FIELD

The present disclosure relates to a tensile specimen, in particular a fiber-composite-material tensile specimen, to a method for producing a tensile specimen, to a device for carrying out a tensile test, and to a method for carrying out a tensile test.

BACKGROUND

Although any desired types of tensile tests can be used, the present disclosure and the problem addressed thereby are explained in greater detail in relation to high-speed tensile tests using fiber-composite tensile specimens.

Sometimes, for high-speed tensile tests, there are clamping designs which are predominantly suitable for metal tensile specimens. Projections of this type are described for example in FAT [*Forschungsvereinigung Automobiltechnik*—Research Association of Automotive Technology] Series No. 211 by the Research Association of Automotive Technology with the title "Dynamic material characteristics for crash simulation", AiF [*Arbeitsgemeinschaft industrieller Forschungsvereinigungen*—German Federation of Industrial Research Associations] No. 14205.

Accordingly, for example what are known as parallel clamping chucks are used, in which a tensile specimen is clamped in parallel clamping jaws with a prestressing force. Furthermore, there are what are known as "fast biters", in which the parallel clamping jaws grip only after an acceleration path, wherein teeth of the clamping jaws dig into the specimen, which requires the specimen to have a metallically ductile surface.

Furthermore, there are projections, wherein metal wedges, which are known as cap strips, are screwed or adhered, and optionally also bolted or riveted, onto a planar and straight specimen made of fiber composite material. In the tensile test, the metal wedges cooperate with corresponding clamping jaws.

SUMMARY

A problem addressed by the present disclosure is that of providing an improved clamping concept for tensile specimens, in particular for fiber-composite-material tensile specimens.

The following is accordingly provided:
a tensile specimen, in particular a fiber-composite-material tensile specimen, comprising: a test portion which comprises a fiber material and a tensile stress direction which is predetermined for a material test; and a force-introduction portion, wherein the fiber material in the force-introduction portion extends at least in part along a face which is oriented obliquely to the tensile stress direction;
a method for producing a fiber-composite-material tensile specimen, comprising the following method steps: inserting a strand comprising fiber material in a shaping mold, wherein the fiber material is formed by a straight fiber portion and an oblique fiber portion which is adjacent to the straight fiber portion and extends obliquely thereto; inserting an insert defining an oblique face for the oblique fiber portion in the region of the oblique fiber portion; and curing a matrix material to form a fiber-composite component;
a device for carrying out a tensile test, comprising: a specimen holder body which comprises a force-transmission face for introducing a tensile force into a force-introduction face of a tensile specimen, in particular of a tensile specimen according to the disclosure herein and/or a tensile specimen which is produced by a method according to the disclosure herein; wherein the device has a predetermined tensile test direction, to which the force-transmission face extends obliquely; and wherein the specimen holder body is designed to be longer than a force-introduction portion of the tensile specimen in order to apply a normal force resulting from the tensile force to the tensile specimen in the region of a transition between the force-introduction portion and a test portion; and
a method for carrying out a tensile test, comprising the following method steps: inserting a tensile specimen, in particular a tensile specimen according to the disclosure herein and/or a tensile specimen which is produced by a method according to the disclosure herein, in a device for carrying out a tensile test, in particular a device according to the disclosure herein; applying a tensile force to the tensile specimen via force-transmission faces of the device which extend obliquely to the tensile direction and corresponding force-introduction faces of the tensile specimen; and supporting a normal force resulting from the tensile force and acting on the tensile specimen by an insert which is embedded in the tensile specimen in the region of a force-introduction portion.

The concept on which the present disclosure is based consists in or involves the fact that a tensile specimen containing fiber material, in particular a fiber-composite-material tensile specimen, is already provided with a fiber portion which extends obliquely to the tensile stress direction during the primary shaping or the production thereof for configuring the introduction of force into the tensile specimen in the force-introduction portion thereof, in order to prevent sliding-through in a tensile test by an interlocking fit. Normal force components resulting therefrom and acting on the fiber material locally compress the tensile specimen and thus advantageously prevent a delamination in the region of a transition from the force-introduction portion to the test portion, in particular when the tensile force is introduced very quickly in a high-speed tensile test.

The oblique face, along which the fiber material extends, can be defined in particular by an insert. During the production of a fiber-composite-material tensile specimen, the insert is also embedded in a matrix with which the fiber material is impregnated before the curing.

The fiber material is now arranged in a test portion of the tensile specimen. The fiber material can be a fiber material which is unidirectional in the test portion, which is firstly bent in a direction which extends obliquely to the tensile stress direction at the transition to the force-introduction portion.

Advantageously, according to the disclosure herein, no prestresses are required in the transverse direction, by which crimping or vibration loads of the fiber material are minimized. In the transverse direction, instead, merely the normal force component resulting from the tensile force and, for this purpose, at least approximately proportional normal force component, acts on the tensile specimen. Undesirable stresses in the region of the clamping, in particular in the region of the start of the clamping, and/or the introduction of force are thus reduced. It is thus ensured that the tensile specimen fails in the representative test portion and not in the force-introduction portion.

Furthermore, advantageously, a considerably higher loading capacity can be achieved than with cap strips and/or bolting/riveting, since there is no beginning or seed for a surface removal and/or an internal hole surface.

In addition, a high-speed tensile test can be implemented without any difficulty, since the wedge-shaped force-introduction portion is coupled into a holder in an automatically centered and damped manner after an acceleration phase. Bouncing and/or overshooting during the procedure is additionally dampened or is virtually prevented. A virtually bounce-free force coupling is achieved.

Advantageously, material characteristics, such as modulus of elasticity, elongation at break or resistance to fracture, can thus be detected in a repeatable manner even at high test speeds.

A device for carrying out the tensile test is formed according to the disclosure herein with a force-transmission face which extends obliquely to the tensile test direction, wherein the specimen or specimen holder body, which can receive one or more specimens, is designed to be longer than a force-introduction portion of the tensile specimen in order to apply a normal force resulting from the tensile force to the tensile specimen in the region of a transition between the force-introduction portion and a test portion.

In order to generate the tensile force, the device for high-speed tensile tests can comprise for example a servo-hydraulic drive having an acceleration path, a falling weight or a weight which is accelerated in another manner, in particular by a compressed air cylinder.

For the transmission of the tensile and normal force, preferably an overlay is provided, which is arranged between the tensile specimen and the force-transmission face of the specimen holder body. The overlay can be attached to or integrally formed on the tensile specimen. Alternatively or additionally, it would also be conceivable to attach or integrally form the overlay or another overlay to/on the specimen holder body of the device. Furthermore, it would be conceivable to form the specimen holder body itself in such a way that the body extends directly along the fiber material and follows the shape of the tensile specimen, in particular even in the region of the transition. Thus, the specimen holder body could also be in the shape of an overlay and at least partially fulfil the function thereof of providing a normal force on the transition between the test portion and the force-introduction portion.

In the case of a method according to the disclosure herein, the tensile force is accordingly applied via force-transmission faces of the device which extend obliquely to the tensile direction and corresponding force-introduction faces of the tensile specimen. Thus, a normal force acting on the tensile specimen results from the tensile force. The normal force is supported by the insert which is embedded in the tensile specimen in the region of a force-introduction portion. In particular, depending on the angle of incidence of the force-transmission face, the normal force is equal to a value which is (approximately) proportional to the tensile force.

According to some embodiments of the tensile specimen, the force-introduction portion comprises an insert which is embedded in the fiber material. In particular, the insert is embedded together with the fiber material in a matrix, in particular a resin matrix. The embedding takes place preferably as early as during the primary shaping of the tensile specimen. Advantageously, by the insert and a shaping mold, a course of the fiber material which is defined on both sides can be produced. Furthermore, by the permanently embedded insert, a very rigid change in shape or widening of the tensile specimen is achieved, in particular one which is more rigid than in the case of an overlay which is adhered on the outside, so that sliding-through of the tensile specimen is effectively prevented by a positive fit in a tensile test. The insert can be formed for example from a polymer or from a metal. It is also conceivable to produce the insert using the same material as the matrix. Normal forces acting on the tensile specimen are supported via the insert.

According to some embodiments, the insert has a wedge-shaped, in particular a symmetrical wedge-shaped design. An oblique face is thus provided, along which the fiber material extends. Advantageously, a uniform introduction of force into the fiber material is thus made possible. In another embodiment, it would be conceivable to form the insert with another tapered shape, for example a pyramid shape. Furthermore, it would also be conceivable, for example in the case of a round tensile specimen, to provide the insert with a cone-shaped design.

According to some embodiments, the insert splits the fiber material in the region of the force-introduction portion into at least two strands which extend along different sides of the insert. Advantageously, it is thus possible to introduce force into the fiber material in a manner which is symmetrical on both sides. The fiber material can also be split into more than two strands. For example, in the case of an insert which is in the form of a four-sided pyramid, the fiber material can be split into four strands. Furthermore, in the case of a conical design of the insert, a circumferential split into a plurality of strands along the lateral surface of the cone would be conceivable. In particular, a split into a number of strands which corresponds to the number of fiber filaments of the fiber material is possible.

According to some embodiments, in the region of a transition from the test portion to the force-introduction portion, an external overlay is provided, the inner face of which extends along the fiber material, and the outer face of which forms a force-introduction face for a force introduction of a specimen holder. In the case of a fiber material comprising unidirectional fibers in the test portion, the overlay may extend in parallel with the fiber direction. The overlay advantageously provides for the introduction of a normal force component of the tensile force into the transition region. In particular in a gusset region at which fiber strands divide at the end of the insert, delamination is thus effectively prevented. It is thus ensured that the specimen fails in the test portion and not in the force-introduction portion or in the transition region. Furthermore, the overlay advantageously also allows an external flexible adaptation of the geometry of the tensile specimen to a specimen holder body of a device for carrying out a tensile test.

According to some embodiments, the force-introduction face of the overlay extends from the force-introduction portion over the transition and in part into the test portion. It is thus ensured that the normal force is in the region of the transition in a tensile test. Optionally or additionally, the force-introduction face extends obliquely to the tensile stress direction. In another embodiment which would be suitable in particular for quasistatic tensile tests, it is also conceivable for a course of the force-introduction face to be in parallel with the tensile stress direction. In this case, in particular a normal force which is to be estimated in advance would be provided by prestressing of a specimen holder body of a device for carrying out the tensile test.

According to some embodiments, a respective overlay is arranged on both sides of the tensile specimen. The force-introduction portion in this case forms a wedge shape, in particular a symmetrical wedge shape, together with the overlays. Thus, a symmetrical design is provided, which advantageously allows a symmetrical and uniform introduction of force and effectively prevents sliding-through.

According to some embodiments, the overlay contains a damping material, in particular a damping polymer, preferably polyvinyl chloride (PVC) or polyamide (PA). The polymer can also be a tough resin or a thermoplastic elastomer. Alternatively or additionally, the material can be a plastically or quasi-plastically deforming material which is intended for damping. By the damping material, in particular in the case of high-speed tensile tests, by acting on a specimen holder body of a tensile test device, induced vibrations are effectively damped.

In additional embodiments, metal overlays can also be provided. In one embodiment, the overlay contains a ductile metal. In this case, it is conceivable to use parallel clamping jaws, in particular comprising a corrugation. Damping can be achieved in this case by plastic deformation when a specimen holder body, in particular a corrugated clamping jaw, acts on the ductile metal. In another embodiment, it would be conceivable to construct the overlay as a specimen holder body for direct connection to a device for carrying out a tensile test. In this case, for example the two overlays could be interconnected or interconnectable behind the end of the tensile specimen and comprise a connection portion for fixing to a device for carrying out a tensile test. For example, a connection portion could be in the form of a thread for screwing onto a device for carrying out a tensile test.

In one embodiment of the method for producing a tensile specimen, on a first mold half of the shaping mold, a first strand comprising fiber material is inserted, and on a second mold half of the shaping mold, a second strand comprising fiber material is inserted, wherein the insert is inserted between the first strand and the second strand. Thus, the insert defines an oblique face for the oblique fiber portions on both sides. In a preferred embodiment, the insert has a symmetrical wedge-shaped design so that a symmetrically designed tensile specimen is produced.

According to some embodiments, a step of forming or adding an external overlay is provided, the overlay being arranged on an outer face of the fiber-composite component in the region of the transition between the straight fiber portion and the oblique fiber portion. For this purpose, for example before the insertion of the strand, the overlay can be inserted in the mold and subsequently embedded, adhered after the curing or cast integrally on the fiber-composite component, in particular as a pure matrix portion. Advantageously, the overlay is thus formed during the production of the tensile specimen. Preferably, an overlay is constructed or integrally formed on the two sides of the tensile specimen.

According to some embodiments of the device for carrying out a tensile test, the specimen holder body is designed to transmit force to an overlay, which is attached to or integrally formed on the outside of the tensile specimen and extends over the transition. Advantageously, during the force transmission, a normal force component thus acts on the transition region.

In another embodiment, the specimen holder body itself can extend directly along the fiber material, in particular in the fiber direction, in the region of the transition between the force-introduction portion and the test portion.

According to one embodiment of the method for carrying out a tensile test, in the region of a tapered end of the insert, in particular at a transition from the force-introduction portion to a test portion of the tensile specimen, a normal force acting on the tensile specimen is applied. In particular, the normal force is applied via an overlay which is provided in the region of the transition on the outside of the tensile specimen and forms the force-introduction face.

The configurations and developments above can be combined with one another as desired where appropriate. In particular, features of the tensile specimen can be transferred to the method for producing the tensile specimen, and vice versa. Furthermore, features of the device for carrying out a tensile test can be transferred to the method for carrying out the tensile test, and vice versa. Furthermore, features of the tensile specimen and features of the device for carrying out a tensile test can be transferred to a test arrangement for carrying out a tensile test comprising such a device and a tensile specimen of this type.

Further possible configurations, developments and implementations of the disclosure herein also do not comprise explicitly mentioned combinations of features of the disclosure herein described previously or in the following with respect to the embodiments. In particular, in the process a person skilled in the art will also add individual aspects as improvements or additions to the respective basic form of the present disclosure.

BRIEF DESCRIPTION OF THE DRAWINGS

The disclosure herein will be described in greater detail below on the basis of embodiments with reference to the accompanying figures of the drawings. The elements of the drawings are not necessarily shown to scale with respect to one another.

In the drawings:

FIG. 7A is a schematic side view of a stationary specimen holder body;

FIG. 7B is a schematic front view of the stationary specimen holder body;

FIG. 8 is a schematic front view of a movable specimen holder body;

In the figures, the same reference numerals denote like or functionally like components, unless stated otherwise.

DETAILED DESCRIPTION

Figure 1:
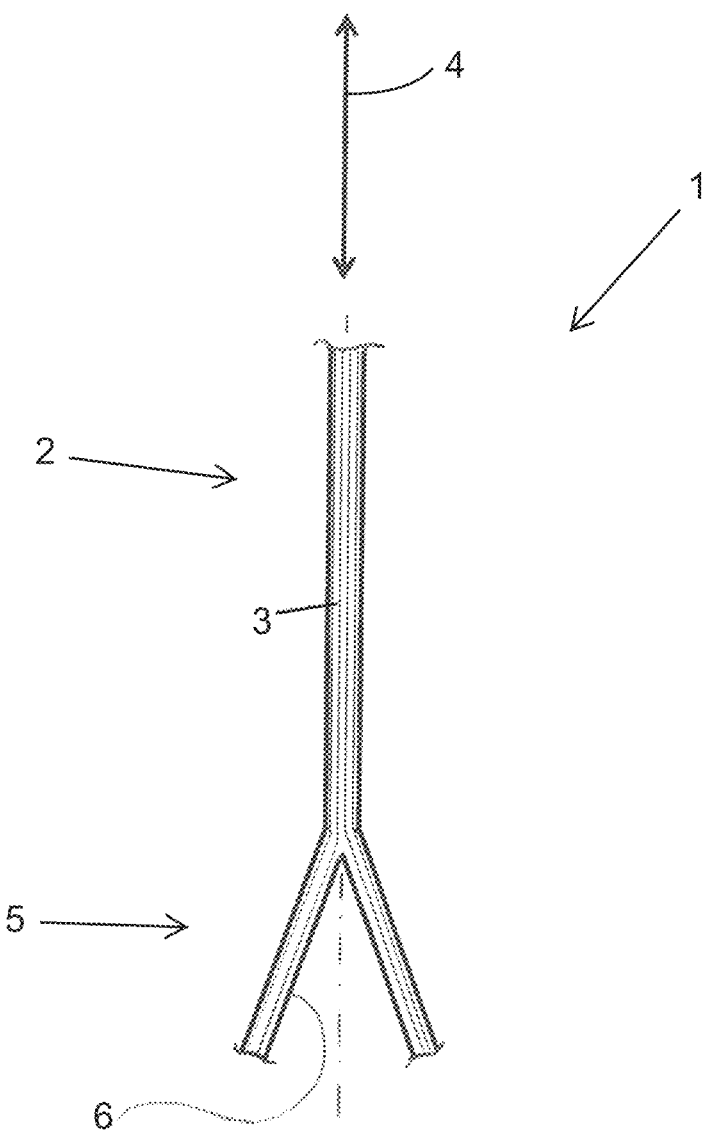
FIG. 1 is a schematic view of a detail of a tensile specimen.

FIG. 1 is a schematic view of a detail of a tensile specimen 1. A detail is shown which shows one end of a tensile specimen 1.

The tensile specimen 1 comprises a test portion 2 and a force-introduction portion 5. The test portion 2 is formed directly along and/or in parallel with a tensile stress direction 4, for which the tensile specimen 1 is designed. The test portion 2 contains a fiber material 3, which, in the region of the test portion 2, comprises fibers which extend in a preferably unidirectional manner in the tensile stress direction 4.

The fiber material 3 further extends into the force-introduction portion 5 and is divided or split there into two strands, which each extend along a face 6 which is oriented obliquely to a tensile stress direction 4.

Figure 2:
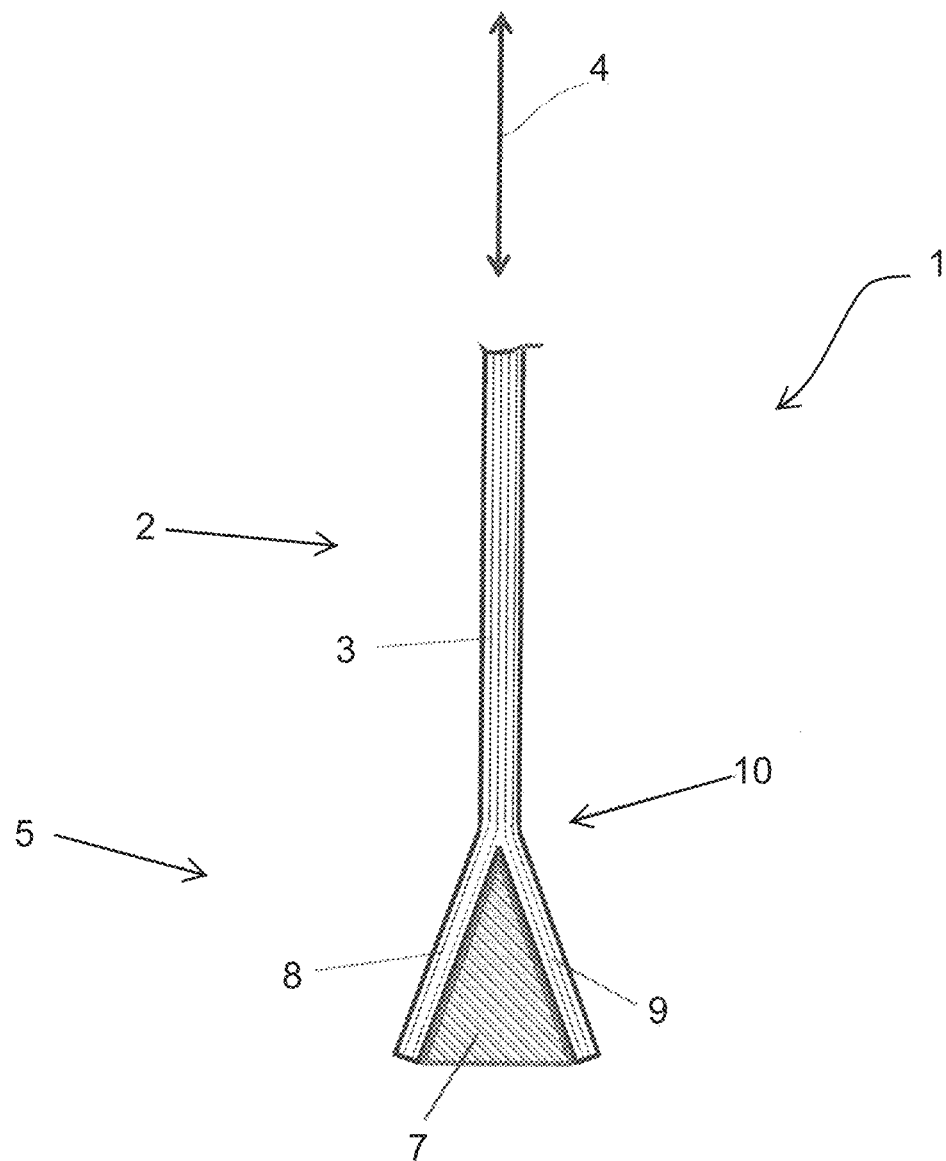
FIG. 2 is a schematic view of a detail of a tensile specimen comprising an insert.

FIG. 2 is a schematic view of a detail of a tensile specimen 1 comprising an insert 7.

The insert 7 has a symmetrical wedge-shaped design and divides or splits the fiber material 3 in the region of the force-introduction portion 5 into two 2 strands 8, 9, which each extend along a face which is oriented obliquely to the tensile stress direction 4. The two strands 8, 9 accordingly extend along two different sides of the insert 7.

Between the test portion 2 and the force-introduction portion 5, there is a transition 10, at which a tip of the insert 7 ends, and the fiber material 3 splits into the strands 8 and 9.

Figure 3:
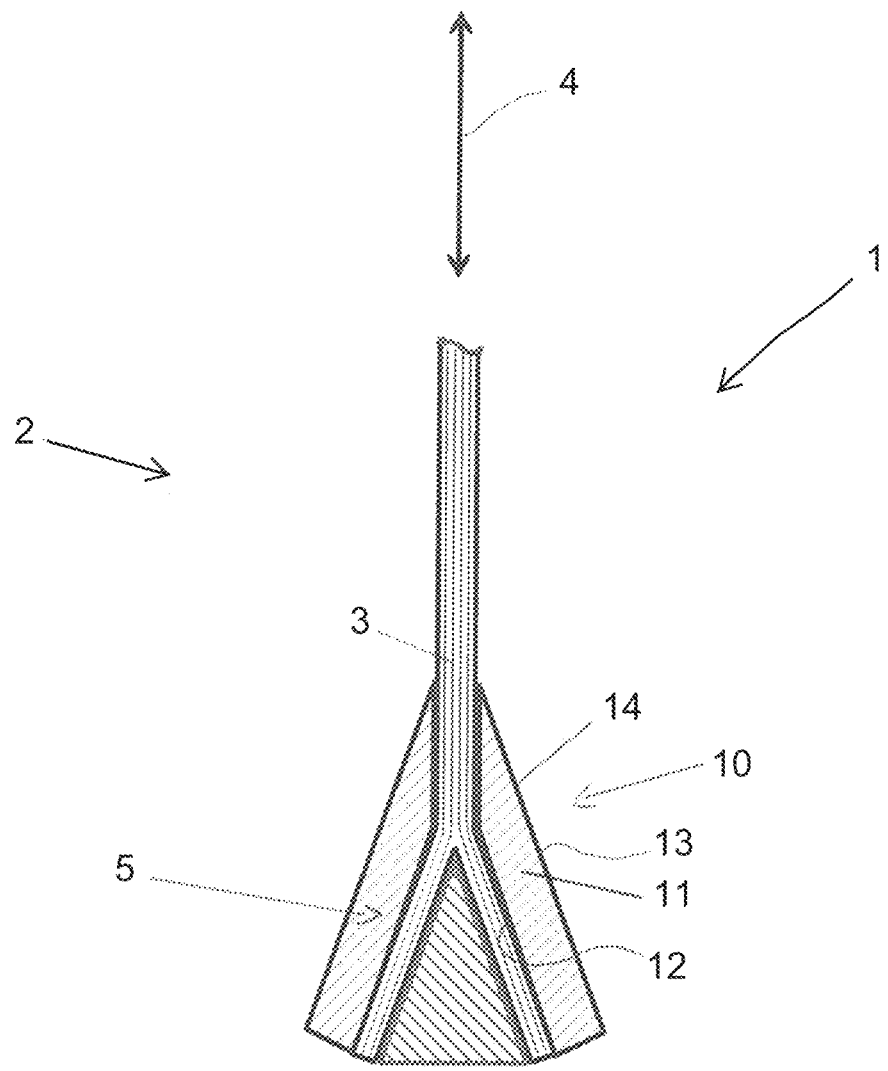
FIG. 3 is a schematic view of a detail of a tensile specimen comprising overlays.

FIG. 3 is a schematic view of a detail of a tensile specimen 1 comprising overlays 11.

A respective overlay 11 is attached to or integrally formed on both sides of the tensile specimen 1 shown in FIG. 2 on the outside thereof. The overlay covers the region of the transition 10, and the inner face 12 thereof extends along the fiber material 3 or in the fiber direction. In the region of the test portion 2, the overlay thus follows the unidirectional fibers extending along the tensile stress direction 4 and, in the force-introduction portion, along the strands 8, 9 extending obliquely thereto.

Together, the force-introduction portion 5 and the two overlays 11 form a symmetrical wedge shape.

On the outer face 13, the overlays 11 each provide a planar force-introduction face 14, which extends obliquely to the tensile stress direction 4. The face extends over the entire length of the force-introduction portion 5 and over the transition 10 as far as the test portion 2. The force-introduction face 14 is used to introduce a tensile force into the tensile specimen 1, in particular via a force-transmission face which is provided on a specimen holder body and corresponds to the force-introduction face 14.

The overlays 11 preferably contain a damping material. The material is in particular a damping polymer, such as polyvinyl chloride or polyamide. Tough resins are also considered.

In one possible embodiment, damping can be achieved by a desired plastic deformation during application of force, in particular with no or with only a few resilient portions. For example polymers are used, the typical stress/strain curves of which have a considerable quasiplastic range.

In this case, by way of example, the overlay 11 is made entirely of the damping material. However, in another embodiment, the overlay can also contain only a layer or a portion of the damping material.

Figure 4:
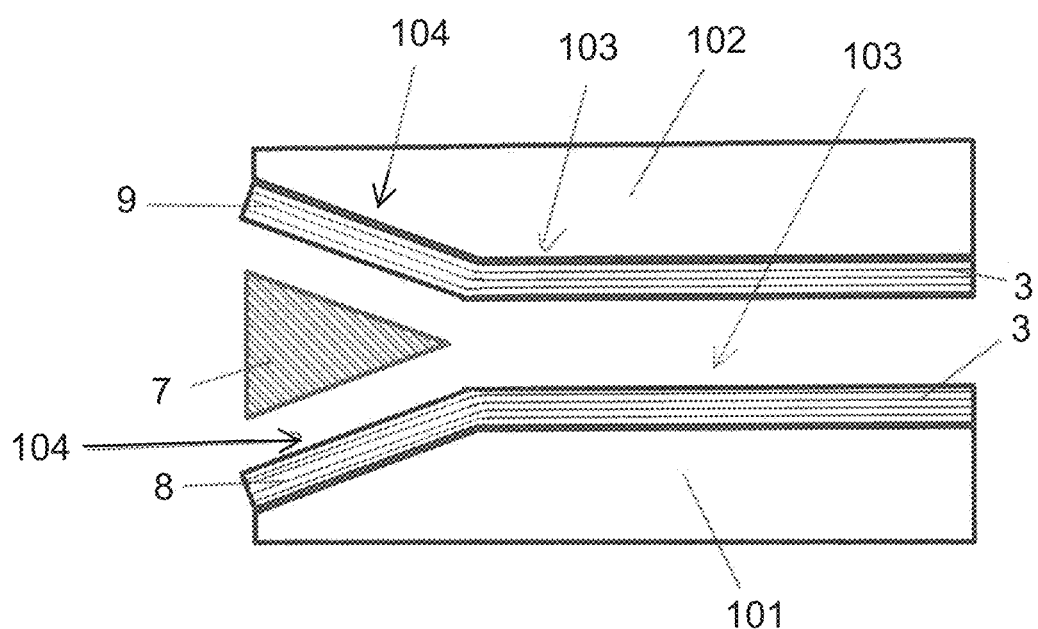
FIG. 4 is a schematic view of an arrangement for producing a tensile specimen comprising an insert.

FIG. 4 is a schematic view of an arrangement for producing a tensile specimen 1 comprising an insert 7. The drawing shows a detail of the arrangement in the region of an end of a tensile specimen 1.

In this case, a shaping mold comprising a first mold half 101 and a second mold half 102 is provided. In order to produce a tensile specimen 1, in each case a fiber material 3 is applied to the two mold halves 101, 102. The fiber material 3 is shaped by the shape of the mold halves 101, 102 in each case by a straight fiber portion 103 and an oblique fiber portion 104 which is adjacent to the straight fiber portion 103 and extends obliquely thereto.

The insert 7 is inserted between the oblique fiber portions 104. In this case, when inserted, the insert 7 defines the oblique faces 6 for the oblique fiber portions 104 on the inner face thereof.

After the insert 7 has been inserted and the mold halves 101, 102 have been joined, the fiber material 3, provided that it is a dry fiber material, is infiltrated with a matrix. In this case, the insert 7 is embedded in the matrix material. The matrix material is subsequently cured under pressure and heat in order to produce a fiber-composite component 105.

The fiber-composite component 105 is in the form of a tensile specimen according to FIG. 2.

Figure 5:
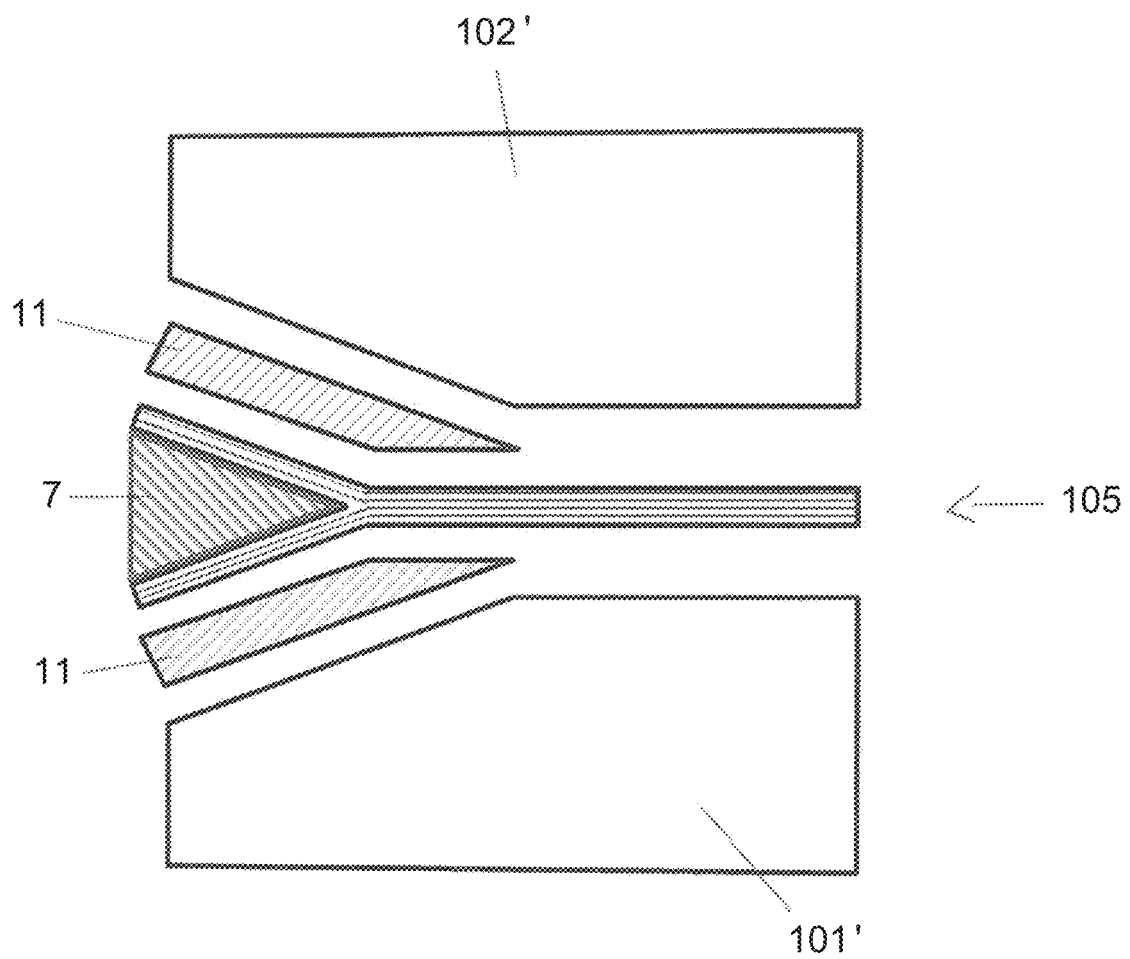
FIG. 5 is a schematic view of an arrangement in the case of the production of a tensile specimen comprising overlays.

FIG. 5 is a schematic view of an arrangement in the case of the production of a tensile specimen comprising overlays 11.

In the embodiment shown by way of example, a fiber-composite component 105 which is produced as described with reference to FIG. 4 is inserted, together with the two separately produced overlays 11 which are arranged on both sides of the component on the outside thereof, in another shaping mold which is adapted to the shape of the overlays 11 and comprises a first mold half 101' and a second mold half 102'. A resin or an adhesive is provided between the overlays 11 and the fiber-composite component 105, wherein the overlays 11 are adhered, in particular under pressure and/or heat, to the fiber-composite component 105 in the region of the oblique fiber portions 104 and of a transition from the oblique to the straight fiber portion 103.

Alternatively, it would also be conceivable to insert the fiber-composite component 104 without the overlays 11 in the mold comprising the mold halves 101', 102' and to produce the overlays 11 by pouring out the mold or by cavities provided in the region of the overlays 11 which are drawn in FIG. 5. In this case, the overlays 11 are cast integrally on the fiber-composite component 105.

In yet another embodiment, the overlays 11, the fiber material 3 and the insert 7 together, in particular when dry, can be inserted in the mold halves 101', 102' and infiltrated in the same production step, and subsequently cured under pressure and temperature. The production of a fiber-composite component 105, which is shown in FIG. 4, would be omitted as an intermediate step in this case.

Figure 6:
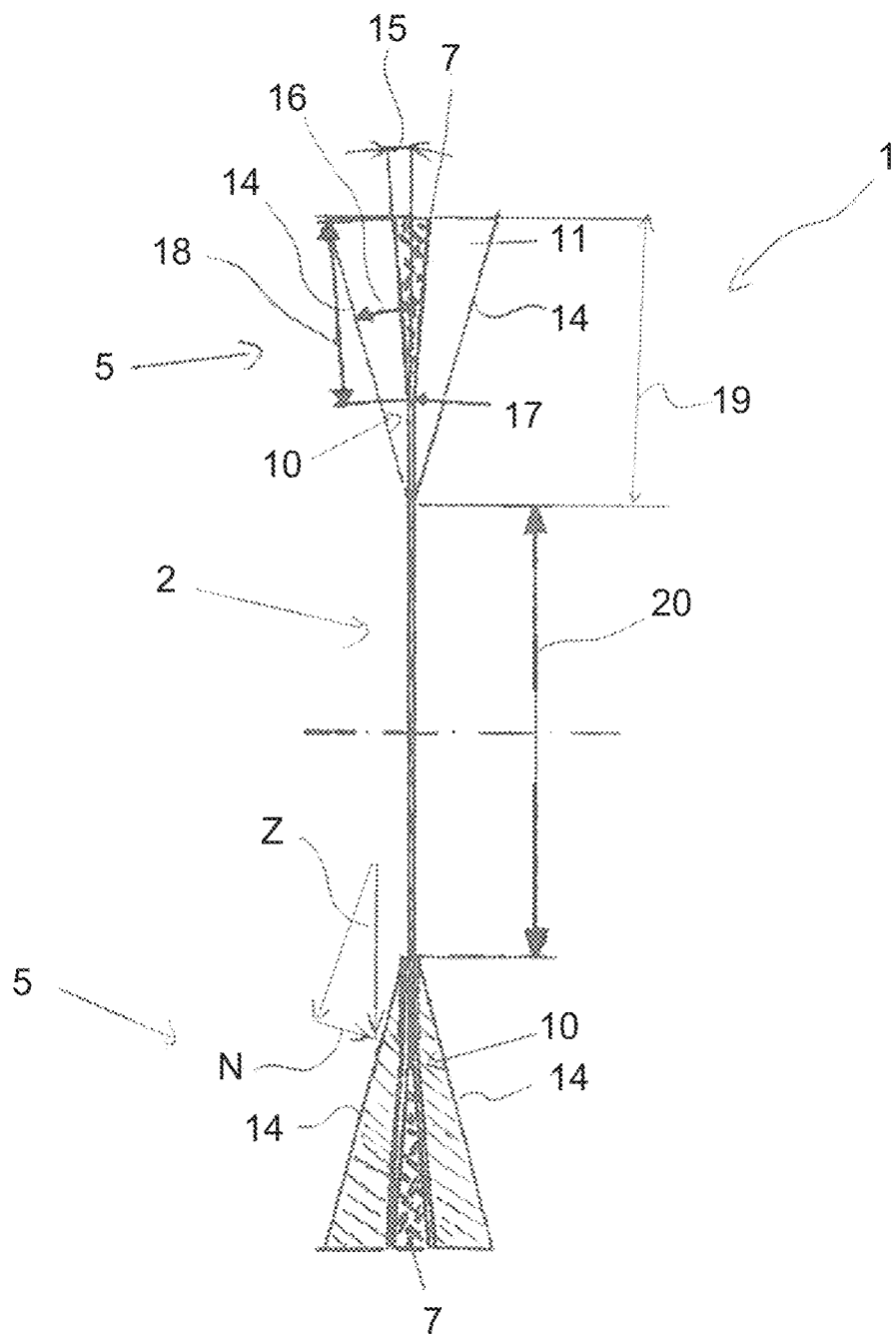
FIG. 6 is a schematic view of a complete tensile specimen.

FIG. 6 is a schematic view of a complete tensile specimen 1. Accordingly, the two ends of a tensile specimen 1 are shown schematically. The ends are each designed as shown in detail in relation to FIG. 3.

The inserts 7 each have an apex angle 15 which is formed so as to be less than an apex angle 16 of the overlays 11. Furthermore, the inserts 7 each have a length 18 which is formed so as to be less than a length 19 of the overlays 11.

The overlays 11 can be formed with a small radius 17 in the region of the transition, which radius preferably corresponds to the radius of the fibers of the fiber material 3 in this region. For example, such a radius lies in the range of from 1 to 2 cm.

The test portion 2 of the tensile specimen 1 connects the two force-introduction portions 5. The test portion 2 starts in each case at the transition 10 to the force-introduction portion 5 and is thus covered at the ends thereof in each case by the overlays 11. Thus, an actual test length 20 of the tensile specimen 1 is shorter than the test portion 2. However, by the overlays 11, it is ensured that the tensile specimen 1, as desired in a tensile test, fails in the region of the test length 20 and not at the transitions 10.

In order to carry out a tensile test, a tensile force Z is introduced into the tensile specimen 1 at the force-introduction faces 14 of the overlays, in parallel with the tensile stress direction 4 of the test portion 2, as shown by way of example on one of the overlays 11. As a result of the fact that the force-introduction faces 14 are oriented obliquely to the tensile force Z, a normal force component N, which is generated by the tensile force Z and is also shown in the drawings, is produced, which acts on the tensile specimen 1 in the region of the force-introduction portion 5 and of the transition 10 and locally compresses the tensile specimen 1. This normal force or compression is desirable in order to prevent delamination or removal of the fiber material of the insert 7, in particular in the region of the transition 10. The value of the normal force N in this case is approximately proportional to the value of the tensile force Z. A deviation from an ideal proportionality can result from friction which is present on the force-introduction faces.

FIG. 7A is a schematic side view of a stationary specimen holder body 201. FIG. 7B is a schematic front view of the stationary specimen holder body 201.

The specimen holder body 201 is part of a device 200 for carrying out a tensile test.

The specimen holder body 201 comprises a receiving portion 205 and a connection portion 206. The receiving portion 205 is designed to receive clamping jaws, which are constructed in the form of tensioning wedges 207. The tensioning wedges 207 are attached to the receiving portions 205 by screws.

The connection portion 206 is in the form of a thread for connection to a load cell 209 and/or to an acceleration device 210.

FIG. 8 is a schematic front view of a movable specimen holder body.

The fundamental construction of the movable specimen holder body 202 corresponds to the construction of the stationary specimen holder body 201. However, by contrast with the stationary specimen holder body 201, the movable specimen holder body 202 comprises an extended receiving portion 205. The extended receiving portion 205 acts as an acceleration path for accelerating a tensile specimen 1 which is received therein before the clamping wedge 207 acts on the tensile specimen 1.

Figures 9A, 9B:
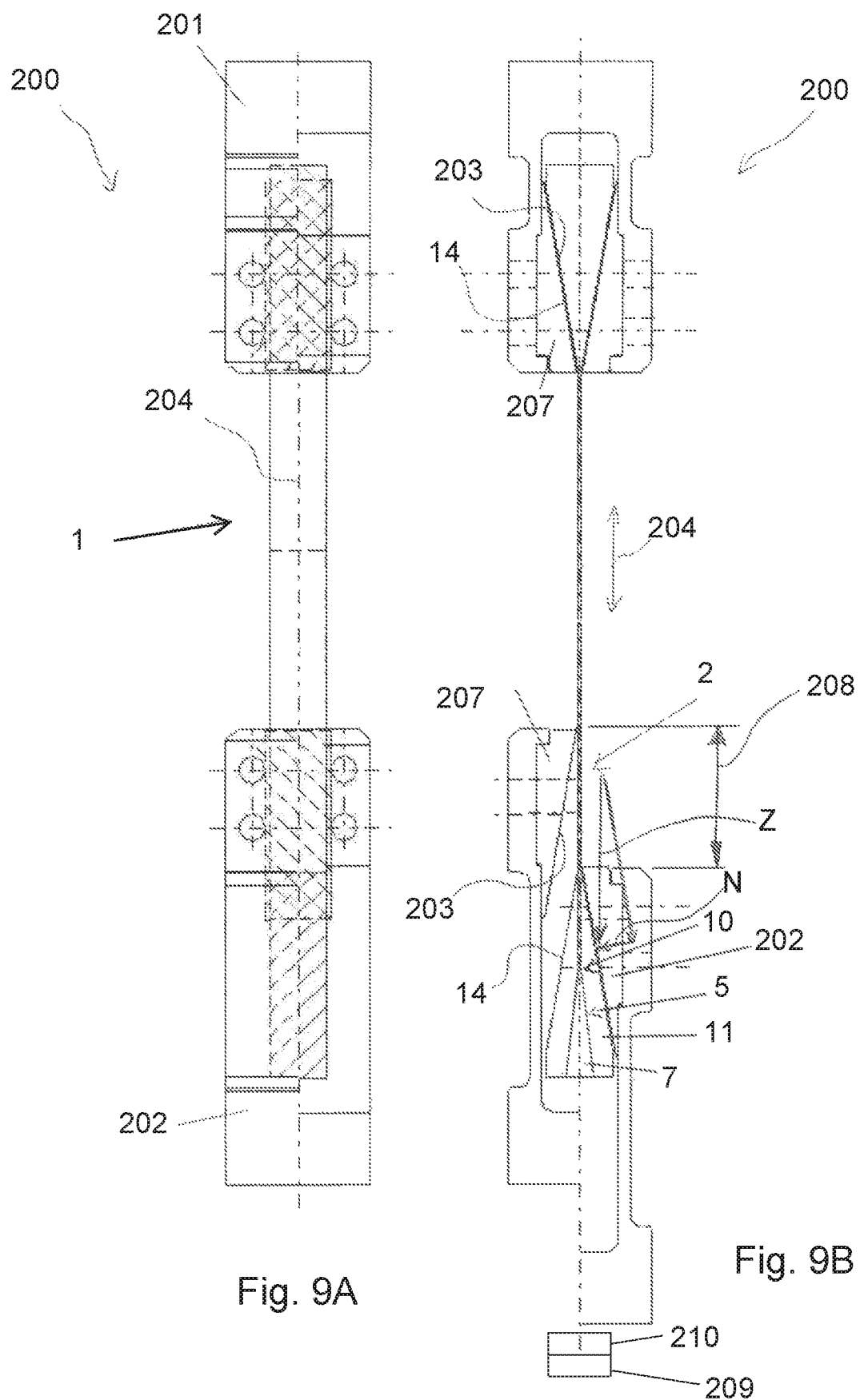
FIG. 9A is a schematic side view of a device for carrying out a tensile test.
FIG. 9B is a schematic front view of the device for carrying out a tensile test.

FIG. 9A is a schematic side view of a device 200 for carrying out a tensile test. FIG. 9B is a schematic front view of the device 200.

A tensile specimen 1 is received or inserted in the device 200. A test arrangement from a tensile test is thus shown here.

The stationary specimen holder body 201 is arranged as shown above. The movable specimen holder body 202 is shown at the bottom. An inverted arrangement of the specimen holder bodies 201, 202 or a horizontal arrangement of the specimen holder bodies 201, 202 is also possible.

The tensile specimen 1 is received in the specimen holder bodies 201, 202. In particular, in this case, the tensile specimen 1 is a tensile specimen according to FIG. 6.

The tensile specimen 1 is in the form of a planar tensile specimen, and therefore has a greater width in the side view in FIG. 9A than in the front view according to FIG. 9B.

FIG. 9A exclusively shows the movable specimen holder body 202 in a stationary state before an acceleration thereof.

In the stationary state, the force-introduction portion 5 of the tensile specimen 1 is arranged in the extended receiving portions 205 of the movable specimen holder body 202. In this case, the force-introduction portion 5 does not cooperate with the tensioning wedges 207, but rather is at a distance therefrom which corresponds to the length of the acceleration path 208.

The left side of FIG. 9B shows the stationary state, and the right side shows a moved state, in which the specimen holder body 202 has been accelerated over the acceleration path 208 and applies a tensile force Z acting in the tensile test direction 204 to the tensile specimen 1.

In order to generate the tensile force, the device 200 comprises, for high-speed tensile tests, for example a servo-hydraulic drive 210 comprising an acceleration path. Alternatively, a falling weight or a weight which is accelerated in another manner, in particular by a compressed air cylinder, can be provided.

The tensile force Z is applied to the force-introduction face 14 of the tensile specimen or the overlays 11 thereof via a force-transmission face 203 of the tensioning wedges 207 which extends obliquely to the tensile test direction 204. In this case as well, as explained with reference to FIG. 6, due to the oblique force-transmission face 203, resulting from the tensile force Z, a normal force N is applied to the tensile specimen, in particular in the region of the transition 10 between the force-introduction portion 5 and the test portion 2. The normal force is supported by the insert 7.

At the oblique force-transmission faces 203 and force-introduction faces 14, in the tensioned state, a force fit and an interlocking fit are produced between the specimen holder body 202 and the tensile specimen 1.

FIG. 10A to 10D show holders from a tensile test in various stages.

Figures 10A, 10B, 10C, 10D:
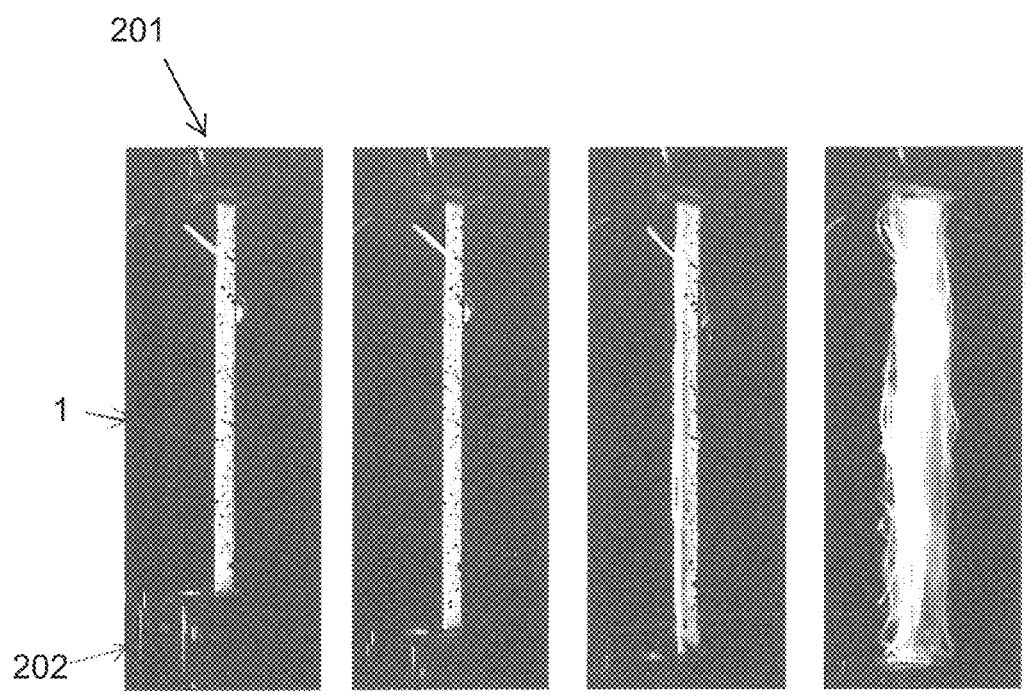
FIGS. 10A to 10D show holders from a tensile test in various stages.

FIG. 10A shows a test arrangement in the stationary state, as described with reference to FIG. 9A.

FIG. 10B shows a moved state, in which a tensile force acts on the tensile specimen 1, as described with reference to FIG. 9B.

FIG. 10C shows the tensile specimen 1 in an already considerably extended state, wherein first appearances of failure start in the test portion 2 at the lateral edge of the tensile specimen 1.

FIG. 10D shows the tensile specimen 1 at the end of the tensile test after a complete failure or fracture in the region of the test portion 2.

Figure 11:
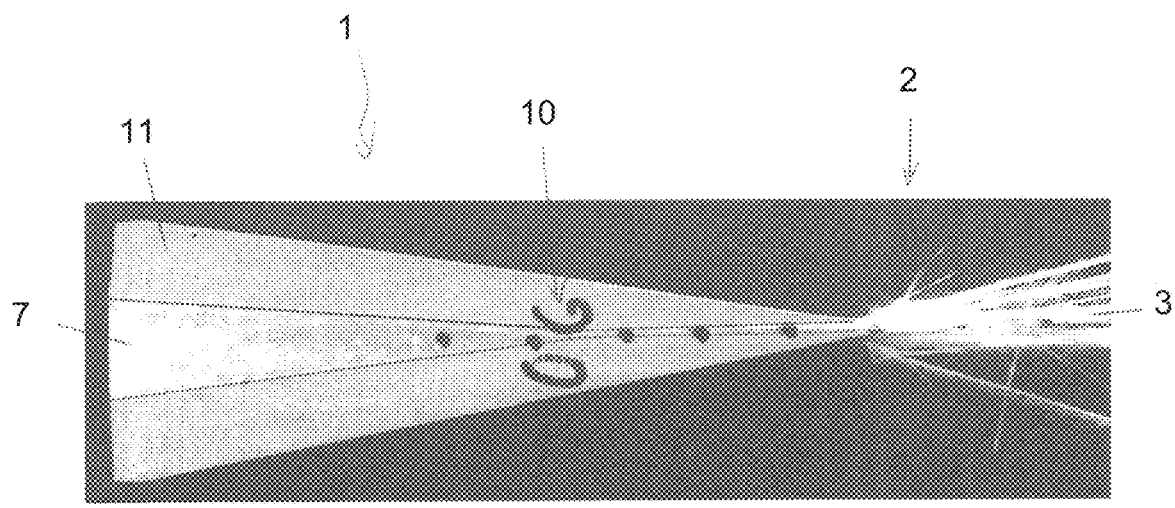
FIG. 11 is a lateral detailed view of a tensile specimen after the tensile test.

FIG. 11 is a lateral detailed view of a tensile specimen after the tensile test. The drawing shows a detail in the region of the transition 10.

The torn-open fiber material 3 in this case shows that the tensile specimen 1 fails in the region of the test portion 2 after the projection of the overlay 11, but is undamaged in the region of the transition 10 between the force-introduction portion 5 and the test portion 2, which is covered by the overlay 11.

Figure 12:
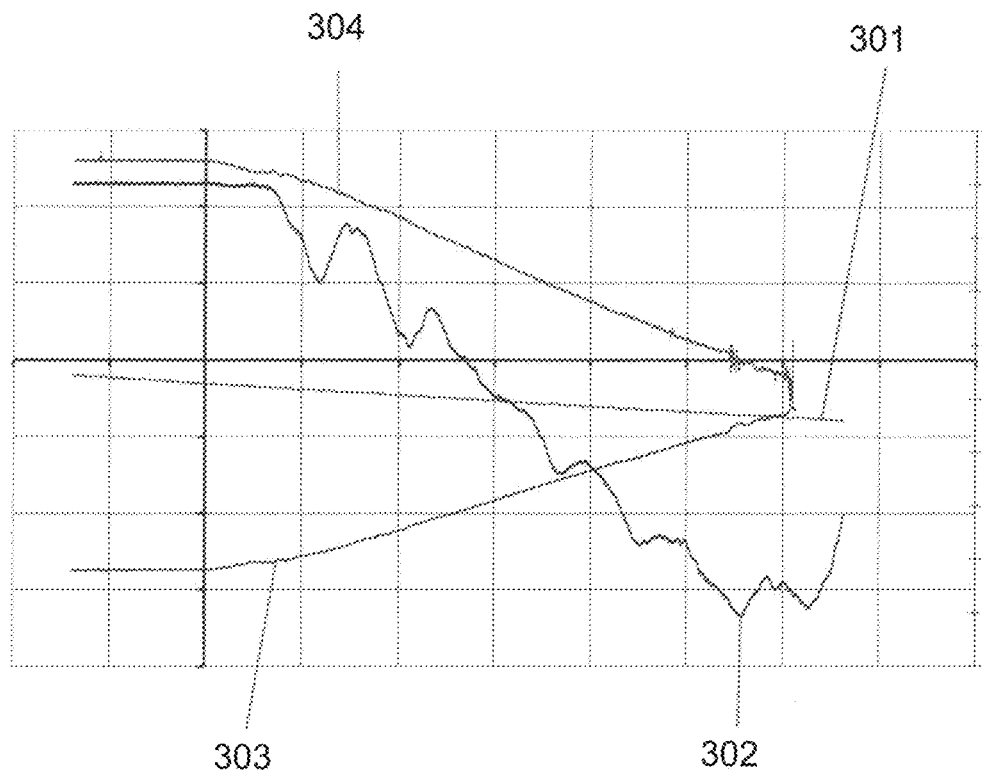
FIG. 12 shows a measurement curve from a high-speed tensile test.

FIG. 12 shows a measurement curve from a high-speed tensile test.

In this case, the courses of a movement 301 of the tensile specimen over time are shown, wherein the measurement values are shown over the time plotted on the x-axis.

A movement 301 of the tensile specimen during the tensile test and a force signal 302 which is measured by a piezoelectric sensor are shown. Although the force signal has slight vibrations, the vibrations are within an extent which is suitable for test evaluation.

Furthermore, a longitudinal expansion 303 and a transverse expansion 304 which are measured in the course of the tensile test on the tensile specimen by strain gauges are applied.

Figure 13:
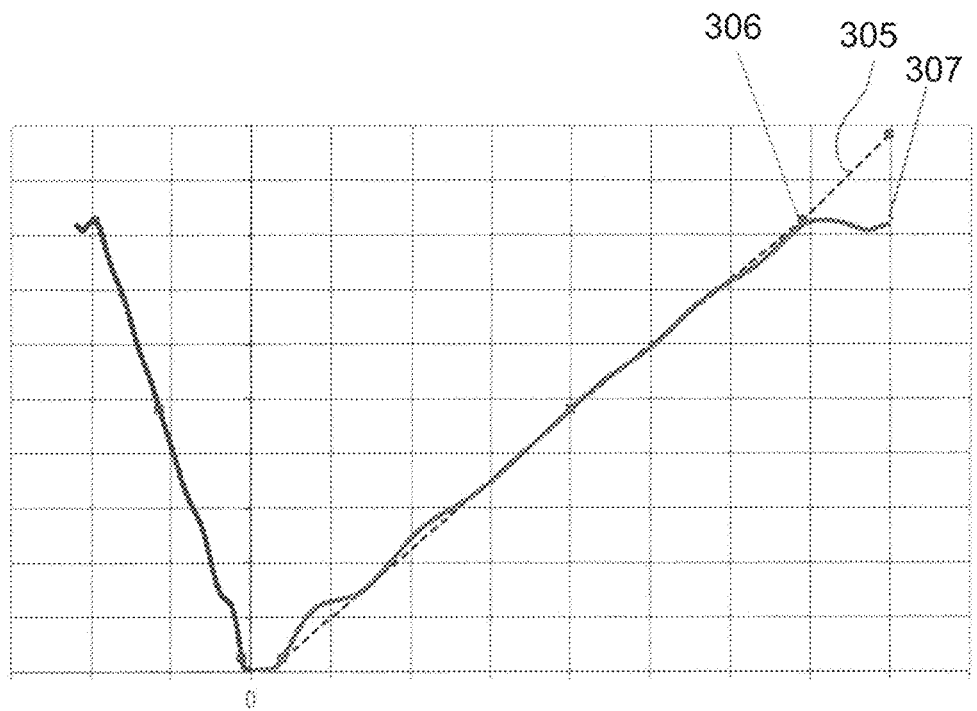
FIG. 13 shows a stress/strain curve of the high-speed tensile test.

FIG. 13 shows a stress/strain curve of the high-speed tensile test. The curve is a measurement curve after a suitable smoothing or filtering of the measured data.

The tension is applied over the expansion. Proceeding from a 0 expansion, a negative expansion is applied in the transverse direction of the tensile specimen to the left, and a positive expansion is applied in the longitudinal direction of the tensile specimen to the right.

A dashed line shows a straight line 305 by Hooke's law which results from the measurement curve, the gradient of which line forms the modulus of elasticity of the material.

Furthermore, a yield point 306 can be detected, at which a plastic deformation of the material of the tensile specimen begins. A fracture of the tensile specimen begins in this case after a short region of plastic expansion of the material at one end 307 of the curve.

Figure 14:
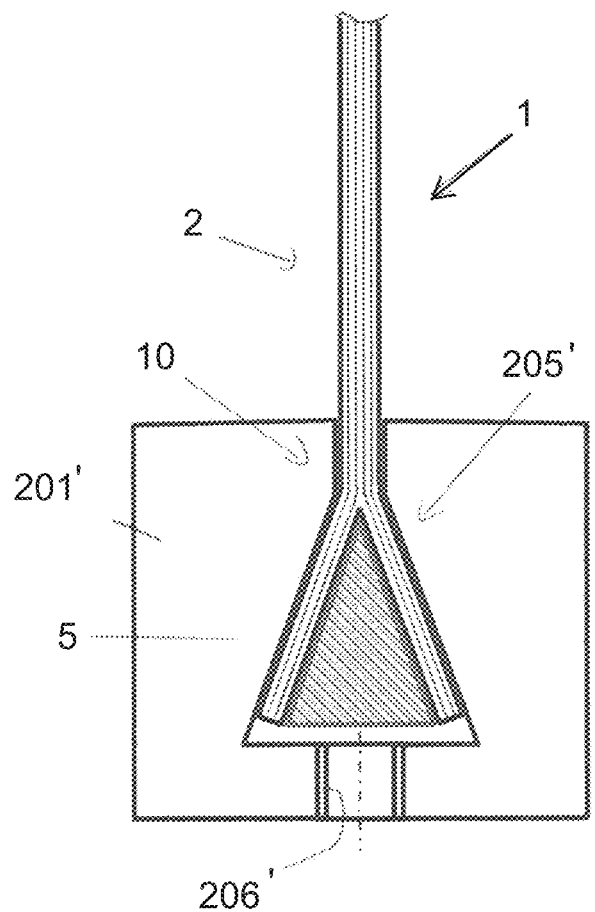
FIG. 14 is a schematic view of a specimen holder body comprising a received tensile specimen according to another embodiment.

FIG. 14 is a schematic view of a specimen holder body 201' comprising a received tensile specimen 1 according to another embodiment.

In this embodiment, it is provided to clamp the tensile specimen 1 in a specimen holder body 201' without any overlays. Instead, the receiving region 205' of the specimen holder body 201' in this case clings to the tensile specimen 1 continuously from the force-introduction portion 5 over the transition 10 as far as the test portion 2. A tensile force can be applied via the connection portion 206' which is provided behind the end of the tensile specimen 1.

Such embodiments are suitable for example for tensile tests having very high test speeds, in which there is a risk of sliding-through or failure in the region of the clamping for conventional tensile specimen geometries comprising fiber-composite materials. In particular, it is possible to use such an arrangement in a test arrangement which is conventionally referred to as a "Split-Hopkinson pressure bar", in which a mass is accelerated to a high speed by a compressed air cylinder. In this case, the connection portion 206' provides compatibility with a test arrangement of this type.

In another embodiment, it would be conceivable to construct an overlay 11 as a specimen holder body 201 for direct connection to a device for carrying out a tensile test. In this case, for example the two overlays 11 could be made of metal and could be interconnected or interconnectable behind the end of the tensile specimen 1. In this case, there is also a connection portion in the region of the connection of the two overlays 11, which connection portion is for example in the form of an inner thread, for fixing to a device for carrying out a tensile test.

Although the present disclosure has been described on the basis of preferred embodiments, it is not restricted to the embodiments, but rather can be modified in various ways.

For example, the design of the insert 7 as a wedge and the division of the fiber material 3 into two strands are to be understood as being given purely by way of example. It would also be conceivable to design an insert with another symmetrical shape, for example as a pyramid, and to divide the fiber material into another plurality of strands, for example in the case of a four-sided pyramid, into four strands. Furthermore, in particular in the case of a round tensile specimen, it would be conceivable to design the insert 7 as a cone and to provide a circumferential split of the fiber material 3 along the lateral surface of the cone.

As an alternative to a polymer overlay, it would be conceivable to provide the overlay so as to be made of a ductile metal in order to provide improved frictional locking with a specimen holder body. Damping could take place in this case by plastic deformation of the ductile material. In this case, it would also be conceivable, for quasistatic tensile tests, to form the force-introduction face in parallel with the tensile stress direction, for example in order to cooperate with conventional parallel clamping jaws.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a", "an" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

What is claimed is:

1. A fiber-composite tensile test specimen, comprising:
a substantially planar test portion comprising fiber material extending in a tensile stress direction which is predetermined for a material test; and
two force-introduction portions disposed on opposite ends of the test portion, the fiber material extending in each force-introduction portion at least in part along a planar face which is oriented obliquely to a plane defined by the planar test portion.

2. The tensile test specimen of claim 1, wherein each force-introduction portion comprises an insert which is embedded in the fiber material.

3. The tensile test specimen of claim 2, wherein the insert has a wedge-shaped design.

4. The tensile test specimen of claim 3, wherein the insert has a wedge-shaped design symmetric to the planar test portion.

5. The tensile test specimen of claim 2, wherein the insert splits the fiber material in a region of the force-introduction portions into at least two strands which extend along opposite sides of the insert.

6. The tensile test specimen of claim 1, wherein, in a region of a transition from the test portion to each force-introduction portion, an external overlay is provided, an inner face of which extends along the fiber material, and an outer face of which forms a force-introduction face for a force introduction of a specimen holder.

7. The tensile test specimen of claim 6, wherein, for each force-introduction portion, the force-introduction face of the overlay extends from the force-introduction portion over the transition and in part into the test portion and/or extends obliquely to the tensile stress direction.

8. The tensile test specimen of claim 6, wherein, for each force-introduction portion, a respective overlay is arranged on both sides of the tensile test specimen, and/or the force-introduction portion forms a wedge shape together with the overlay(s).

9. The tensile test specimen of claim 6, wherein the overlay contains a damping material.

10. The tensile test specimen of claim 9, wherein the damping material comprises polyvinyl chloride or polyamide.

11. A device for carrying out a tensile test, the device comprising:
   a moveable specimen holder body and a stationary specimen holder body, each comprising a force-transmission face for introducing a tensile force into a force-introduction face of a planar tensile specimen, the device having a predetermined tensile test direction; and
   an acceleration device,
   wherein each specimen holder body is longer than the respective force-introduction portion of the tensile specimen in order to apply a normal force resulting from the tensile force to the tensile specimen in a region of a transition between the force-introduction portion and a central test portion, and
   wherein each force-transmission face extends in a plane oriented obliquely to a plane defined by the planar tensile specimen.

12. The device of claim 11, wherein the specimen holder body is configured to transmit force to an overlay which is attached to or integrally formed on the outside of the tensile specimen and extends over the transition.

13. A method for carrying out a tensile test, comprising:
   inserting a tensile specimen in a device for carrying out a tensile test, the tensile specimen comprising:
      a substantially planar test portion comprising a fiber material extending in a tensile test direction;
      two force-introduction portions disposed on opposite ends of the test portion, the fiber material extending in each force-introduction portion at least in part along a planar face which is oriented obliquely to a plane defined by the planar test portion; and
      an insert embedded in a region of each force-introduction portion;
   applying a tensile force to the force-introduction portions of the tensile specimen via force-transmission faces of the device which extend obliquely to the tensile test direction and correspond to force-introduction faces of the tensile specimen; and
   supporting a normal force resulting from the tensile force and acting on the tensile specimen by the insert.

14. The method of claim 13, comprising, in a region of a tapered end of the insert, applying a normal force acting on the tensile specimen.

15. The method of claim 14, wherein a normal force acting on the tensile specimen is applied at a transition from the force-introduction portions to a test portion of the tensile specimen via an overlay which is provided in a region of the transition on the outside of the tensile specimen, which overlay forms the force-introduction face.

* * * * *